(12) United States Patent
Pacetti et al.

(10) Patent No.: US 6,527,863 B1
(45) Date of Patent: Mar. 4, 2003

(54) SUPPORT DEVICE FOR A STENT AND A METHOD OF USING THE SAME TO COAT A STENT

(75) Inventors: Stephen D. Pacetti, San Jose, CA (US); Plaridel K. Villareal, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/895,533

(22) Filed: Jun. 29, 2001

(51) Int. Cl.[7] ............................................. B05C 13/02
(52) U.S. Cl. ..................... 118/500; 623/1.46; 623/1.47; 623/1.48; 606/194; 269/48.1; 269/52
(58) Field of Search ................................ 118/500, 502; 427/2.24, 2.25, 2.28, 2.3; 623/1.1, 1.11, 1.45, 1.46, 920, 1.47, 1.48; 606/194; 269/48.1, 52; 248/314, 201

(56) References Cited

U.S. PATENT DOCUMENTS

| 4,733,665 A | 3/1988 | Palmaz |
| 4,800,882 A | 1/1989 | Gianturco |
| 4,886,062 A | 12/1989 | Wiktor |
| 5,897,911 A | 4/1999 | Loeffler ............... 427/2.25 |

Primary Examiner—Laura Edwards

(57) ABSTRACT

A support device for a stent and a method of coating a stent using the device are provided.

17 Claims, 6 Drawing Sheets

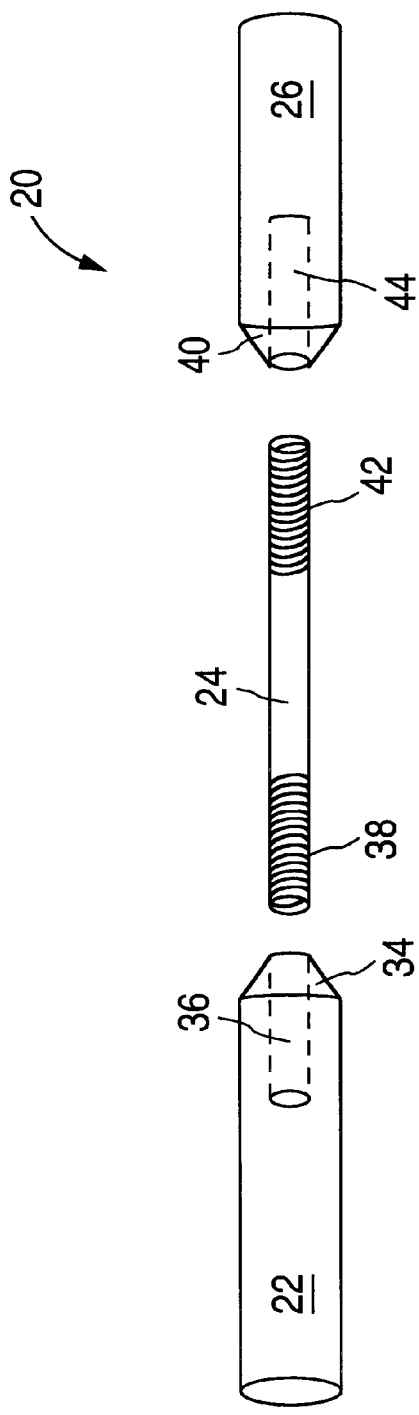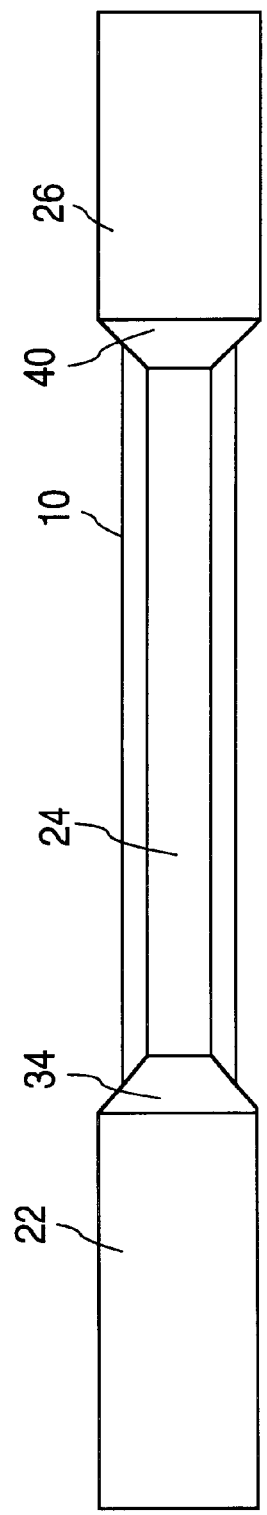

SUPPORT DEVICE FOR A STENT AND A METHOD OF USING THE SAME TO COAT A STENT

BACKGROUND OF THE INVENTION

1. Field of the Invention

This invention relates to a support device for a stent and a method of coating a stent using the device.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway. Typically, stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent surfaces a coating of the polymer and the therapeutic substance impregnated in the polymer.

A shortcoming of the above-described method of medicating a stent is the potential for coating defects. While some coating defects can be minimized by adjusting the coating parameters, other defects occur due to the nature of the interface between the stent and the apparatus on which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the coating from the stent and leaving bare areas. Alternatively, the excess coating may stick to the stent, thereby leaving excess coating as clumps or pools on the struts or webbing between the struts.

Thus, it is desirable to minimize the interface between the stent and the apparatus supporting the stent during the coating process to minimize coating defects. Accordingly, the present invention provides for a device for supporting a stent during the coating application process. The invention also provides for a method of coating the stent supported by the device.

SUMMARY OF THE INVENTION

In accordance with one aspect of the invention a support device for a stent is provided. In one embodiment, the support device includes a body having a first end and a second end and at least three sides extending from the first end to the second end, wherein the three sides are capable of penetrating at least partly into one end of a stent. Any of the sides can have a variety of geometrical configurations such as having a radius of curvature or being V-shaped.

In accordance with another embodiment of the invention, an apparatus for supporting a stent during a process of applying a coating material to the stent is provided. The apparatus includes a first member having an end configured to penetrate at least partially in one end of a stent; and a second member having an end configured to penetrate at lease partially in the opposing end of the stent. Each of the ends can comprise two non-parallel sides for allowing the stent to rest on the ends during the process of applying the coating material. A third member can be included and adapted to extend through the stent for connecting the first member to the second member.

In accordance with another embodiment of the invention a device for supporting a stent includes a structure of a variable size so as to allow a section of the structure to penetrate into a first end of the stent until the size of the structure prevents the structure from penetrating deeper into the first end of the stent. The section of the structure that is capable of penetrating into the first end of the stent includes a surface that is in contact with the stent such that the surface that is in contact with the stent does not extend around the entire perimeter of the section.

A second structure of a variable size can also be provide so as to allow a section of the second structure to penetrate into a second, opposing end of the stent until the size of the structure prevents the structure from penetrating deeper into the second end of the stent. The section of the second structure that is capable of penetrating into the second end of the stent includes a surface that is in contact with of the stent such that the surface that is in contact with the stent does not extend around the entire perimeter of the section of the second structure.

In one variation, the second structure is capable of being moved towards or away from the structure for releasably pinching the stent between the structure and the second structure.

In accordance with another aspect of the invention, a method can also be provided for depositing a coating substance on the stent supported by any one the various described embodiments of the present invention. The coating material can be applied by a spray process or by immersing the stent in the coating material. The coating material can comprise a polymer mixed a fluid and optionally a therapeutic substance added thereto.

BRIEF DESCRIPTION OF THE FIGURES

FIG. 3 illustrates an expanded perspective view of the mounting assembly, in accordance with one embodiment of the present invention.

FIG. 4 illustrates the interface between the mounting assembly and the stent in accordance with one embodiment of the present invention.

DETAILED DESCRIPTION

Embodiments of the Mounting Assembly

Figure 1:
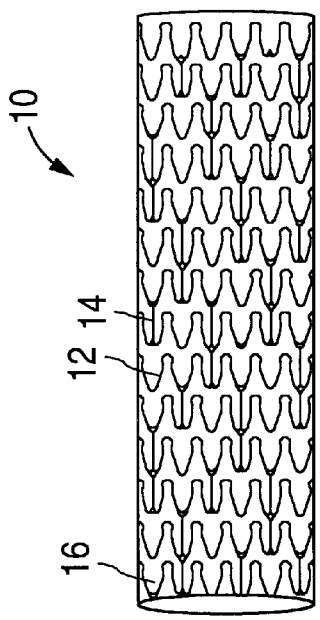
FIG. 1 illustrates a conventional stent.
Figure 2:
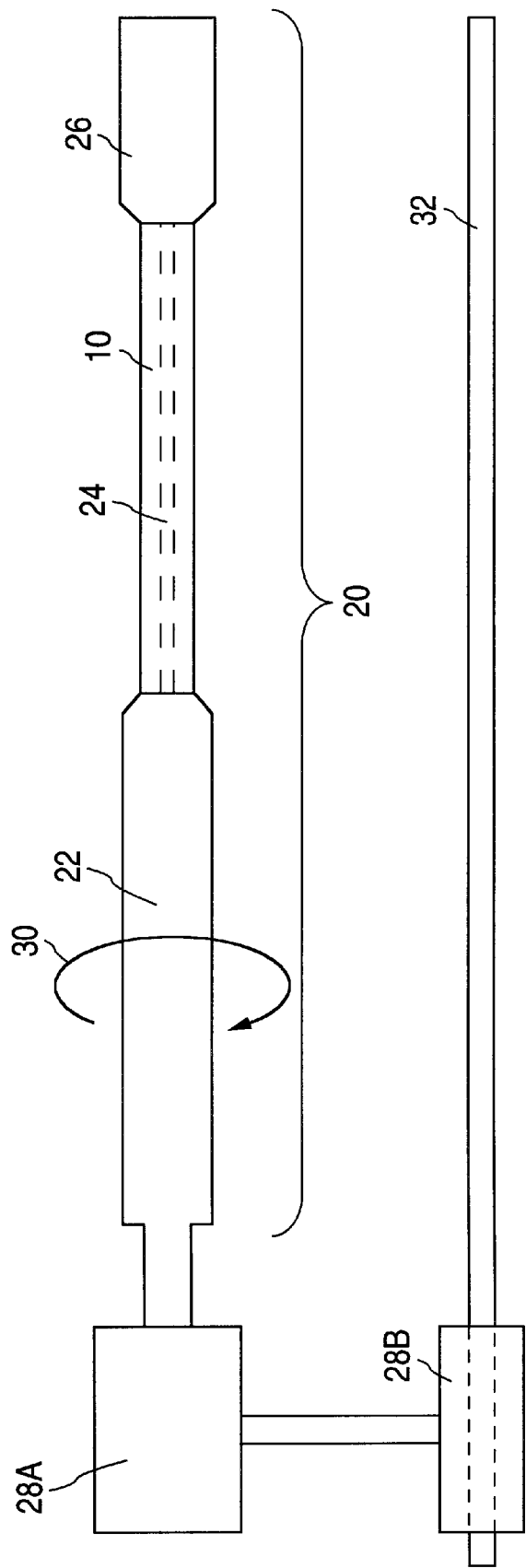
FIG. 2 illustrates a mounting assembly for supporting a stent.

Referring to FIG. 2, a mounting assembly 2 for supporting stent 10 is illustrated to include a first member 22, a mandrel 24, and a second member 26. First member 22 can connect to a motor 28A so as to provide rotational motion about the longitudinal axis of stent 10, as depicted by arrow 30, during the coating process. Another motor 28B can also be provided for moving[] mounting assembly 20 in a linear direction, back and forth, along a rail 32. The type of stent is not of critical significance and the term stent is broadly intended to include stent-grafts or radially expandable stents, such as balloon-expandable stents or self-expandable stents.

Referring to FIG. 3, a first support element 34 can be a part of or disengagably coupled to first member 22. First support element 34 is configured to penetrate at least partially into one end of stent 10, as illustrated in FIG. 4. In accordance with one embodiment, mandrel 24 can be permanently affixed to first support element 34. Alternatively, first member 22 and first support element 34 can include a bore 36 for receiving a first end 38 of mandrel 24. First end 38 of mandrel 24 can be threaded to screw into bore 36. Alternatively, a non-threaded first end 38 of mandrel 24 can be press-fitted or friction-fitted within bore 36. Bore 36 should be deep enough so as to allow mandrel 24 to securely mate with first member 22. The depth of bore 36 can also be over-extended so as to allow a significant length of mandrel 24 to penetrate bore 36. This would allow the length of mandrel 24 to be adjusted to accommodate stents of various sizes.

The outer diameter of mandrel 24 should be smaller than the inner diameter of stent 10 so as to prevent the outer surface of mandrel 24 from making contact with the inner surface of stent 10. A sufficient clearance between the outer surface of mandrel 24 and the inner surface of stent 10 should be provided to prevent mandrel 24 from obstructing the pattern of the stent body during the coating process. By way of example, the outer diameter of mandrel 24 can be from about 0.010 inches (0.254 mm) to about 0.017 inches (0.432 mm) when stent 10 has an inner diameter of between about 0.025 inches (0.635 mm) and about 0.035 inches (0.889 mm).

Second member 26 can include an second support element 40 for penetrating into the opposing end of stent 10 (see FIG. 4). A second end 42 of mandrel 24 can be permanently affixed to second member 26 if end 38 is disengagable from support member 22. Alternatively, in accordance with another embodiment, mandrel 24 can have a threaded second end 42 for screwing into a bore 44 of second member 26. Bore 44 can be of any suitable depth that would allow second member 26 to be incrementally moved closer to first member 22. Accordingly, stents 10 of any length can be securely pinched between first and second members 22 and 26. In accordance with yet another embodiment, a non-threaded second end 42 and bore 44 combination can be employed such that second end 42 is press-fitted or friction-fitted within bore 44 to prevent movement of stent 10 on mounting assembly 20.

As illustrated in FIG. 4, mounting assembly 20 supports stent 10 via support elements 34 and 40. Opposing forces exerted from support elements 34 and 40, for securely pinching stent 10, should be sufficiently strong so as to prevent any significant movement of stent 10 on mounting assembly 20. However, the exerted force should not compress stent 10 so as to distort the body of stent 10. Over or under application of support force can lead to problems such as stent 10 resting too loosely on mounting assembly 20, stent 10 bending and thus contacting mandrel 24, opposing ends of stent 10 flaring on support elements 34 and 40, and increased contact between stent 10 and support elements 34 and 40, all of which can lead to coating defects.

In addition to supporting stent 10 so as to prevent any significant movement of stent 10 on mounting assembly 20 during the coating process, support elements 34 and 40 should provide minimal contact between stent 10 and mounting assembly 20, thereby minimizing the potential for coating defects due to the stent 10-mounting assembly 20 interface.

Figures 5A, 5B, 5C, 5D:
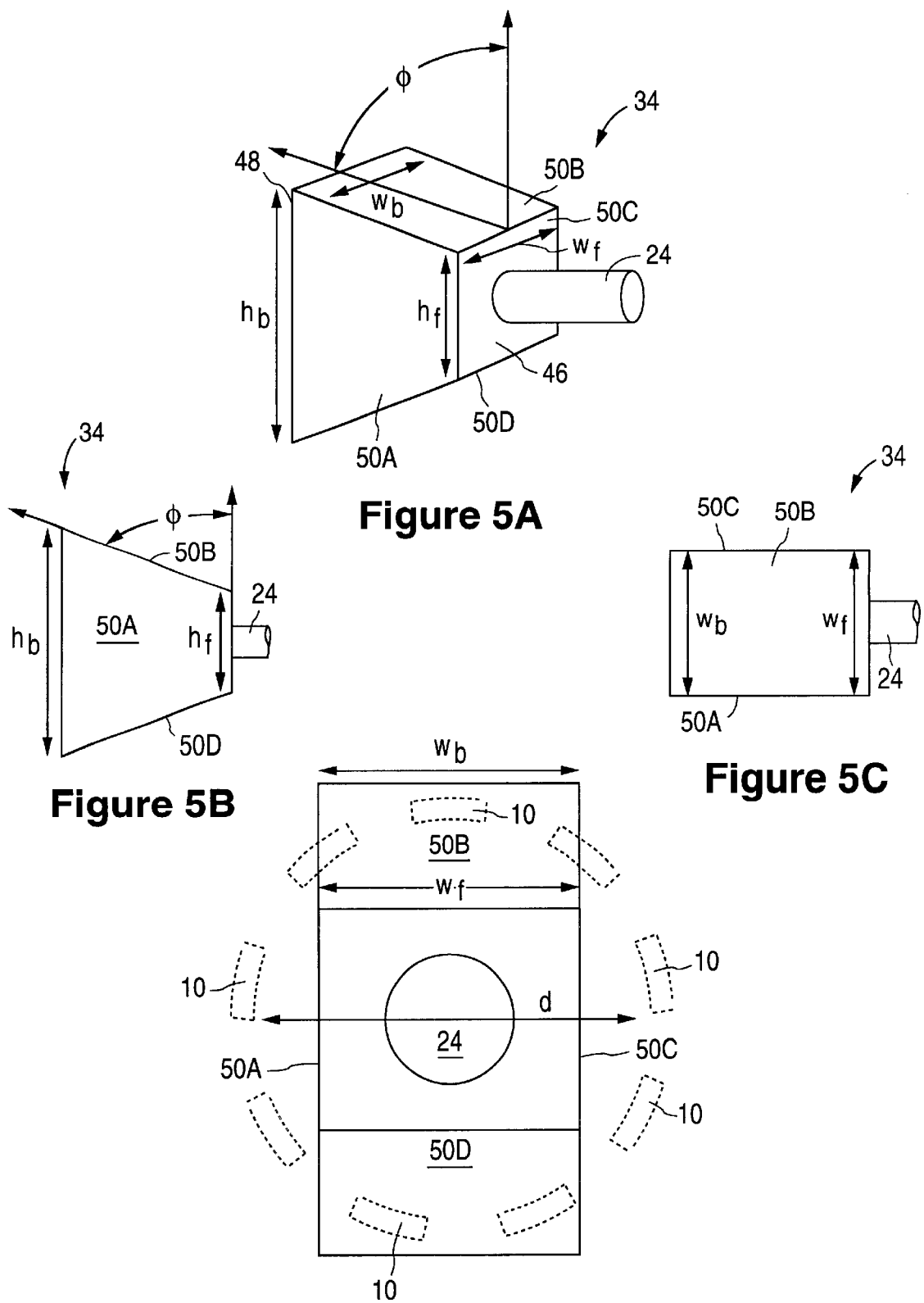
FIGS. 5A–5D illustrate the perspective, side, top and front views of a support element for the mounting assembly in accordance with one embodiment of the present invention.

For ease of discussion, reference will hereinafter be made to first support element 34. However, it is understood that first support element 34 can be identical or substantially similar to second support element 40, and thus, the following discussion of first support element 34 applies equally to second support element 40. In accordance to one embodiment, as illustrated in FIGS. 5A–5D, support element 34 includes a front end 46 and a back end 48 and four sides 50A–50D. In one embodiment, one of the pairs of the opposing sides, such as sides 50B and 50D, can be non-parallel. In other words, the width $w_f$ of front end 46 is equal to the width $w_b$ of the back end, while the height $h_f$ of front end 46 is less than the height $h_b$ of back end 48. Accordingly, sides 50B and 50D taper at an angle $\phi$, which can be from about 15° to about 75°, for example about 45°. Width $W_f$ and height $h_f$ of front end 46 should be smaller than the inner diameter d of the stent employed while height $h_b$ of back end 48 should be larger than the inner diameter d of the stent (the inner diameter refers to the diameter of the stent, whether expanded or unexpanded, as positioned on mounting assembly 20). Accordingly, support element 34 is capable of only partially penetrating into the end of a stent—until the size of the structure prevents support element 34 from penetrating deeper into the stent. FIG. 5D illustrates stent 10 resting on sides 50B and 50D, while sides 50A and 50C do not make contact with stent 10.

Figure 6A:
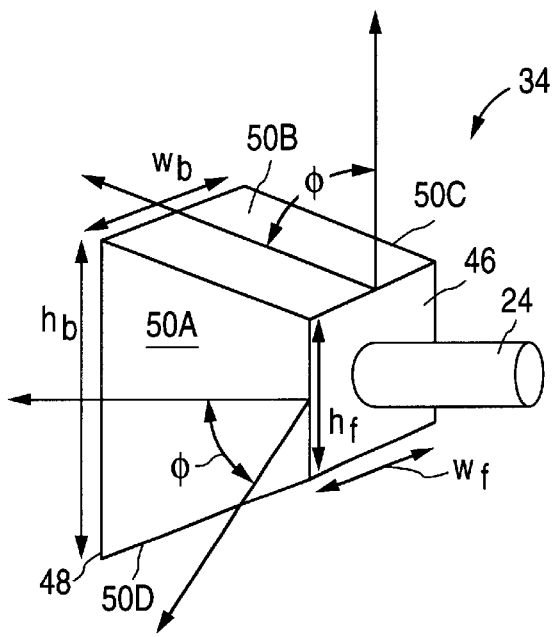
FIGS. 6A and 6B illustrate the perspective and front views of the support element in accordance with another embodiment of the present invention.
Figure 6B:
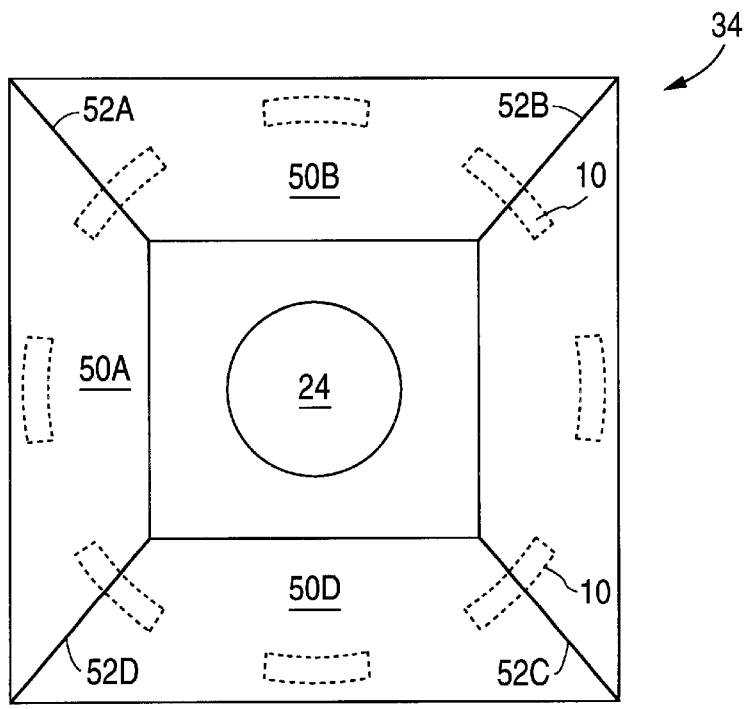

In an alternative variation of FIGS. 5A–5D, in FIGS. 6A and 6B, width $w_f$ can be smaller than width $w_b$, such that each pair of opposing side 50A–50D is non-parallel. As illustrate in FIG. 6B, support element 34 can partially penetrate into the end of stent 10 allowing stent 10 to make contact with and rest on edges 52A–D. Thus minimum contact is made between stent 10 and support element 34.

Figure 7A:
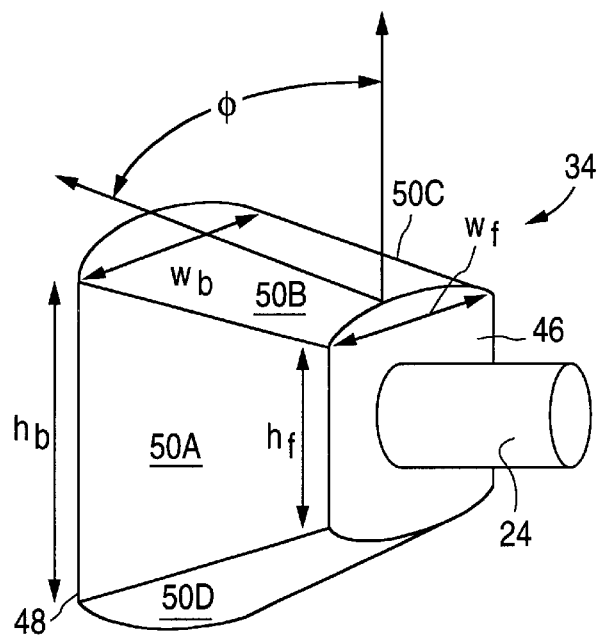
FIGS. 7A and 7B illustrate the perspective and front views of the support element in accordance with another embodiment of the present invention.
Figure 7B:
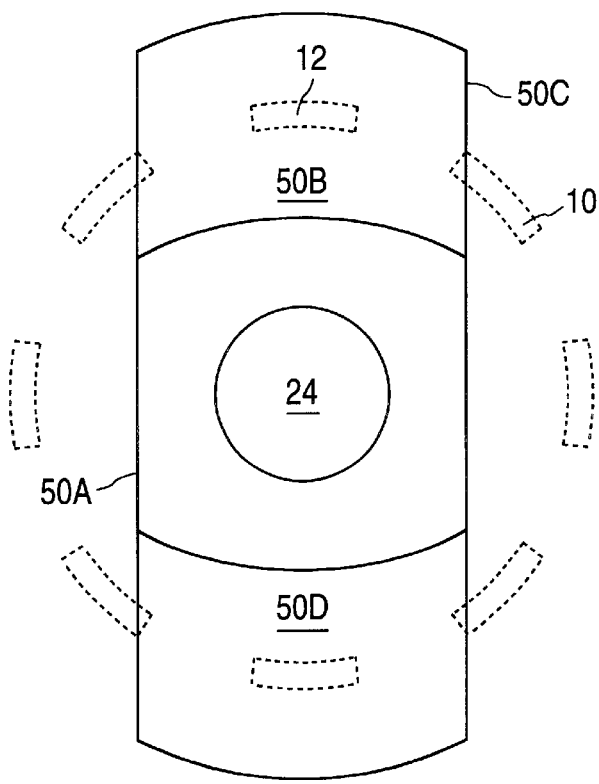

In yet another variation, as illustrated in FIGS. 7A and 7B, sides 50B and 50D can be curved or have a radius of curvature. The radius of curvature of sides 50B and 50D can be the same as the radius of curvature of the inner circumference of the stent so as to allow stent 10 to fittingly rest on sides 50B and 50D.

Figure 8A:
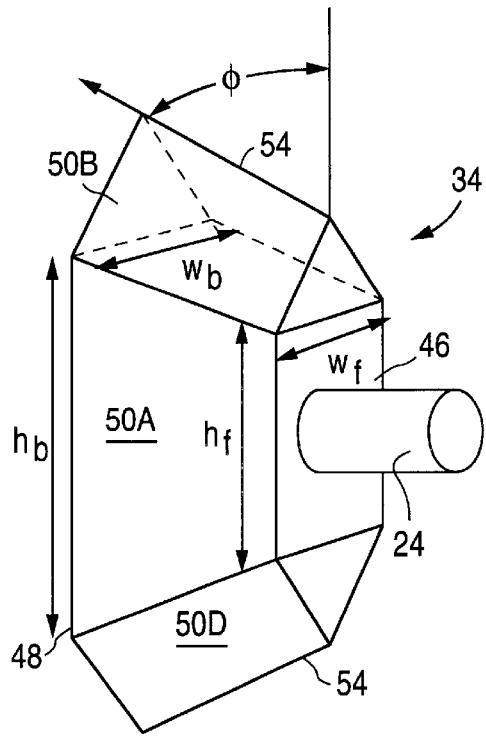
FIGS. 8A, 8B, and 8C illustrate the perspective, side and front views of the support element in accordance with another embodiment of the present invention.
Figure 8B:
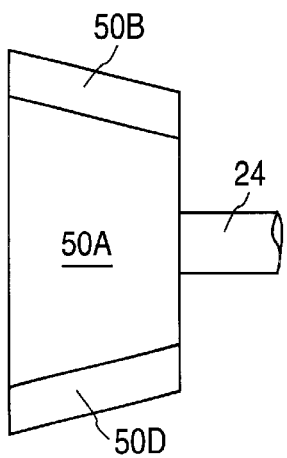
Figure 8C:
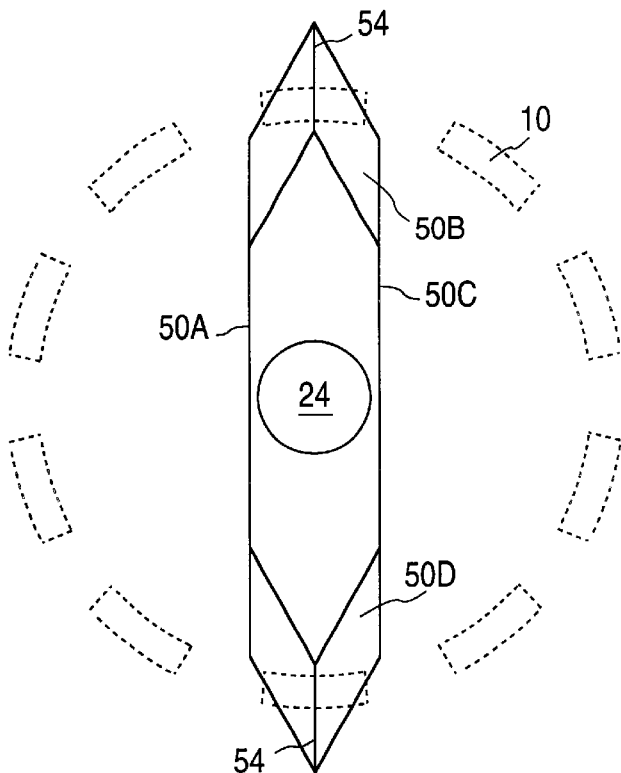

A variety of shapes can be contemplated by one of ordinary skill in the art for support elements 34 and 40. For example, a geometrical configurations such as that illustrated in FIGS. 8A–8C can be employed so as to provide adequate support for a stent without being in too much contact with the stent so as to cause coating defects. FIGS. 8A–8C illustrate nonparallel sides 50B and 50D being V-shaped. Height $h_f$ of front end 46 is less than the height $h_b$ of back end 48 so as to provide a taper at an angle $\phi$, for the V-shaped sides 50B and 50D. Stent 10 will be resting on edges 54 of sides 50B and 50D upon insertion of support element 34 into the end of the stent.

Coating a Stent Using the Mounting Assembly

The following method of application is being provided by way of illustration and is not intended to limit the embodiments of mounting assembly 20 of the present invention. A spray apparatus, such as EFD 780S spray device with VALVEMATE 7040 control system (manufactured by EFD Inc., East Providence, R.I. , can be used to apply a composition to a stent. EFD 780S spray device is an air-assisted external mixing atomizer. The composition is atomized into small droplets by air and uniformly applied to the stent surfaces. The atomization pressure can be maintained at a range of about 5 psi to about 20 psi. The droplet size depends on such factors as viscosity of the solution, surface tension of the solvent, and atomization pressure. Other types of spray applicators, including air-assisted internal mixing atomizers and ultrasonic applicators, can also be used for the application of the composition.

During the application of the composition, a stent supported by mounting assembly 20 can be rotated about the stent's central longitudinal axis. Rotation of the stent can be from about 1 rpm to about 300 rpm, more narrowly from about 50 rpm to about 150 rpm. By way of example, the stent can rotate at about 120 rpm. The stent can also be moved in a linear direction along the same axis. The stent can be moved at about 1 mm/second to about 12 mm/second, for example about 6 mm/second, or for a minimum of at least two passes (i.e., back and forth past the spray nozzle). The flow rate of the solution from the spray nozzle can be from about 0.01 mg/second to about 1.0 mg/second, more narrowly about 0.1 mg/second. Multiple repetitions for applying the composition can be performed, wherein each repetition can be, for example, about 1 second to about 10 seconds in duration. The amount of coating applied by each repetition can be about 0.1 micrograms/cm$^2$ (of stent surface) to about 10 micrograms/cm$^2$, for example less than about 2 micrograms/cm$^2$ per 5-second spray.

Each repetition can be followed by removal of a significant amount of the solvent(s). Depending on the volatility of the particular solvent employed, the solvent can evaporate essentially upon contact with the stent. Alternatively, removal of the solvent can be induced by baking the stent in an oven at a mild temperature (e.g., 60° C.) for a suitable duration of time (e.g., 2–4 hours) or by the application of warm air. The application of warm air between each repetition prevents coating defects and minimizes interaction between the active agent and the solvent. The temperature of the warm air can be from about 30° C. to about 60° C., more narrowly from about 40° C. to about 50° C. The flow rate of the warm air can be from about 20 cubic feet/minute (CFM) (0.57 cubic meters/minute (CMM)) to about 80 CFM (2.27 CMM), more narrowly about 30 CFM (0.85 CMM) to about 40 CFM (1.13 CMM). The warm air can be applied for about 3 seconds to about 60 seconds, more narrowly for about 10 seconds to about 20 seconds. By way of example, warm air applications can be performed at a temperature of about 50° C., at a flow rate of about 40 CFM, and for about 10 seconds. Any suitable number of repetitions of applying the composition followed by removing the solvent(s) can be performed to form a coating of a desired thickness or weight. Excessive application of the polymer in a single application can, however, cause coating defects.

In an alternative method of applying the composition, a stent supported by mounting assembly 20 can be immersed in the composition. The solvent can then be allowed to evaporate from the composition to form a coating on the stent.

Operations such as wiping, centrifugation, or other web clearing acts can also be performed to achieve a more uniform coating. Briefly, wiping refers to the physical removal of excess coating from the surface of the stent; and centrifugation refers to rapid rotation of the stent about an axis of rotation. The excess coating can also be vacuumed off of the surface of the stent.

In accordance with one embodiment, the stent can be at least partially preexpanded prior to the application of the composition. For example, the stent can be radially expanded about 20% to about 60%, more narrowly about 27% to about 55%—the measurement being taken from the stent's inner diameter at an expanded position as compared to the inner diameter at the unexpanded position. The expansion of the stent, for increasing the interspace between the stent struts during the application of the composition, can further prevent "cob web" formation between the stent struts.

In accordance with one embodiment, the composition can include a solvent and a polymer dissolved in the solvent and optionally a wetting fluid. The composition can also include active agents, radiopaque elements, or radioactive isotopes. Representative examples of polymers that can be used to coat a stent include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly (hydroxybutyrate); poly(hydroxybutyrate-co-valerate); polydioxanone; polyorthoester; polyanhydride; poly (glycolic acid); poly(D,L-lactic acid); poly(glycolic acid-co-trimethylene carbonate); polyphosphoester; polyphosphoester urethane; poly(amino acids); cyanoacrylates; poly (trimethylene carbonate); poly(iminocarbonate); copoly (ether esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

A "wetting" of a fluid is measured by the fluid's capillary permeation. Capillary permeation is the movement of a fluid on a solid substrate driven by interfacial energetics. Capillary permeation is quantitated by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. Representative examples of the wetting fluid include, but are not limited to, tetrahydrofuran (THF), dimethylformamide (DMF), 1-butanol, n-butyl acetate, dimethylacetamide (DMAC), and mixtures and combinations thereof.

The active agent can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone.

Examples of radiopaque elements include, but are not limited to, gold, tantalum, and platinum. An example of a radioactive isotope is $p^{32}$. Sufficient amounts of such substances may be dispersed in the composition such that the substances are not present in the composition as agglomerates or flocs.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A support device for a stent, comprising:
    a body having a first end and a second end and at least three sides extending from the first end to the second end, wherein the three sides are capable of penetrating at least partially into one end of a stent for allowing the stent to rest thereon during application of coating material to the stent.

2. The apparatus of claim 1, wherein two of the sides that are facing one another are non-parallel.

3. The apparatus of claim 1, wherein the body comprises four sides, two of the sides which are opposing one another are non-parallel and configured to allow the stent to rest thereon.

4. The apparatus of claim 1, wherein at least one of the sides has a radius of curvature.

5. The apparatus of claim 1, wherein the body comprises four sides, two of the sides which are opposing one another are non-parallel, have a radius of curvature, and configured to allow the stent to rest thereon.

6. The apparatus of claim 1, wherein at least one of the sides is V-shaped.

7. The apparatus of claim 1, wherein the body comprises four sides, two of the sides which are opposing one another are non-parallel, V-shaped, and configured to allow the stent to rest thereon.

8. An apparatus for supporting a stent during a process of applying a coating material to the stent, comprising:
    a first member having an end configured to penetrate at least partially in one end, of a stent; and
    a second member having an end configured to penetrate at least partially in a opposing end of the stent;

wherein each of the ends comprises two non-parallel sides for allowing the stent to rest on the non-parallel sides during the process of applying the coating material.

9. The apparatus of claim 8, additionally comprising a third member adapted to extend through the stent for connecting the first member to the second member.

10. The apparatus of claim 8, wherein at least one of the two non-parallel sides is curved shaped.

11. The apparatus of claim 8, wherein at least one of the two non-parallel sides is V-shaped.

12. The apparatus of claim 8, wherein the non-parallel sides are facing one another.

13. A device for supporting a stent, the stent having an inner surface and an outer tissue contacting surface, comprising:

a structure of a variable size so as to allow a section of the structure to penetrate into a first end of the stent until the size of the structure prevents the structure from penetrating deeper into the first end of the stent, wherein the section of the structure that is capable of penetrating into the first end of the stent includes a surface that is in contact with the stent such that the surface that is in contact with the stent does not extend around an entire perimeter of the section, the structure allowing the stent to rest thereon during application of coating to the stent.

14. The device of claim 13, additionally comprising a second structure of a variable size so as to allow a section of the second structure to penetrate into a second, opposing end of the stent until the size of the structure prevents the structure from penetrating further into the second end of the stent.

15. The device of claim 14, wherein the second structure is capable of being moved towards or away from the structure for releasably pinching the stent between the structure and the second structure.

16. The device of claim 14, wherein the section of the second structure that is capable of penetrating into the second end of the stent includes a surface that is in contact with the stent such that the surface that is in contact with the stent does not extend around the entire perimeter of the section of the second structure.

17. The device of claim 14, additionally including a third structure extending through the stent and connecting the structure to the second structure, wherein the outer surface of the third structure does not contact the inner surface of the stent.

* * * * *

UNITED STATES PATENT AND TRADEMARK OFFICE
CERTIFICATE OF CORRECTION

PATENT NO.    : 6,527,863 B1
DATED         : March 4, 2003
INVENTOR(S)   : Pacetti et al.

Page 1 of 1

It is certified that error appears in the above-identified patent and that said Letters Patent is hereby corrected as shown below:

<u>Column 8,</u>
Line 65, change "end, of" to -- end of --.
Line 67, change "a" to -- an --.

Signed and Sealed this

Ninth Day of September, 2003

JAMES E. ROGAN
*Director of the United States Patent and Trademark Office*